United States Patent [19]

Huizenga et al.

[11] Patent Number: 4,490,139
[45] Date of Patent: Dec. 25, 1984

[54] IMPLANT NEEDLE AND METHOD

[75] Inventors: John R. Huizenga, Mooresville; Lloyd E. Reddix, Indianapolis, both of Ind.

[73] Assignee: Eli Lilly and Company, Indianapolis, Ind.

[21] Appl. No.: 461,912

[22] Filed: Jan. 28, 1983

[51] Int. Cl.³ .............................................. A61M 5/00
[52] U.S. Cl. ..................................... 604/57; 604/264; 604/272
[58] Field of Search ................................... 604/57–64, 604/264, 272–274

[56] References Cited

U.S. PATENT DOCUMENTS 2,711,733 6/1955 Jacaby, Jr. ........................... 604/274
3,921,632 11/1975 Bardani ................................ 604/60

Primary Examiner—Stephen C. Pellegrino
Attorney, Agent, or Firm—Barnes & Thornburg

[57] ABSTRACT

An improved subcutaneous implant needle is formed as a hollow tube having its forward end cut on a plane at an acute angle to the central axis of the tube to form an elliptical opening, and an elliptical outer edge having a sharp forward portion. The forward extremity of the needle is dressed to form cutting edges intersecting at an obtuse angle and forming a central point. The dressed edges have a width preferably less than two-thirds the diameter of the tube, and the adjoining side portions of the elliptical outer edge are rendered unsharp and dulled, as by abrasion such as sandblasting or tumbling in abrasive media. The needle is dimpled at two locations closely adjacent the rear of the opening.

14 Claims, 3 Drawing Figures

IMPLANT NEEDLE AND METHOD

This invention relates to an improved needle for placing implants under the skin of a farm animal and a method of its manufacture.

Implants have been developed to introduce therapeutic agents into the body of an animal for providing a uniform release of drugs over long periods of time. Such implants typically comprise a drug carrier formed of an organopolysiloxane rubber composition (more generally known as silicone rubber) which is non-reactive toward the drug, non-toxic to the body, and known to be compatible with living tissue even after a prolonged implantation period. The drugs are included in the composition in powder or semisolid or liquid form, and generally have appreciable solubility in the polymer composition of the carrier. The drugs are released from the carrier into the body of the animal by diffusion or migration interstitially between the elastomer molecules to the outer surface of the carrier from which they are removed by the animal's body fluid.

Such implants are not eroded by the animal's body fluids and permit the exposure of the animal to the effect of the drug to be terminated at will by removal of the implant. For example, when the drug is a growth stimulant, termination of the exposure of the animal to the effects of the drug permits a livestock owner to rapidly meet the demands of the marketplace by electing to shorten the time between the treatment of the animal with the drug and slaughtering the animal for use.

To provide treatment of animals, for example, with estradiol, and permit the termination of such treatment, the implants used are in rod-like form and have lengths on the order of an inch. The insertion of such implants into the animal's body must frequently take place at a remote site, such as at a livestock ranch or at feeder lots in the field, and must be performed by ranch and field hands frequently under dirty conditions.

Where such implants are used to expose an animal to drugs over a long period, as in the case of growth stimulants such as estradiol, it is of course necessary that the implant remain in the body of the animal. Implants are placed one by one in the animals by inserting the implant preferably under the skin of the animal's ear. Frequently, the animals are dipped or otherwise exposed to liquid materials after the insertion of the implant. Such exposure to liquid generally results in the animal shaking his head, and thus imposing forces on the implant tending to displace it from the animals's ear. Because the animals, after these treatments, are released into the field, it is not desirable or economically feasible to check each animal to assure that the implant has remained in place.

Implants have been inserted under the skin of the animal by hollow steel tubes or needles having their forward ends cut on a plane defining an acute angle with the central axis of the tube, thus forming an elliptical opening surrounded by an elliptical end face which, along its forward sides and end, form a sharp edge with the cylindrical outer surface of the tube. The point of the tube or needle is commonly sharpened to provide an acutely angled point and a pair of sharpened edges extending outward and rearward of the point. With the use of such a needle, it has been found that implants placed subcutaneously in the ear of a farm animal may become dislodged within a short period of time after their implantation. It is believed this loss of the implant is aggravated at least in part by the shaking of the animal's head which seems to be a natural instinct of the animal following its treatment.

In accordance with the present invention, an implant needle can be manufactured by providing a hollow tube of rigid material, for example, stainless steel, grinding the forward end of the hollow tube along a plane at an acute angle to its central axis to form an elliptical end face having an elongated and closed outer edge, and the point can then be honed to provide the sharp point and adjacent angular sharpened edges. To assist in obtaining positive implantation of the implants, the tube or needle is dimpled at two locations closely adjacent the rearward edge of the elliptical end opening, preferably with one dimple located within the length of the opening and the other dimple behind the opening. To help reduce the loss of implants from the animal's body following their implantation, the foremost extremity or point of the cut end is desirably honed or otherwise treated to produce two sharpened edges lying at an obtuse angle and having a total width less than the outside diameter of the tube, preferably less than two-thirds of such diameter. The needle is also treated to reduce the sharpness and blunt the outer edge of the cut end face, especially the diverging side edges of such face which adjoin and extend rearward from the honed point. The blunting treatment is desirably by abrading the side edges, and this may be done by tumbling the needles with an abrasive media or by sandblasting. When sandblasting is used, the needles may be held in a support which covers the honed point and its adjacent angular sharp edges but exposes the side edges of the elliptical end face, so that the honed point and angular edges are shielded from the abrasion and remain sharp.

The accompanying drawing illustrates the invention and shows an embodiment exemplifying the best mode of carrying out the invention as presently perceived. In such drawings.

Figure 1:
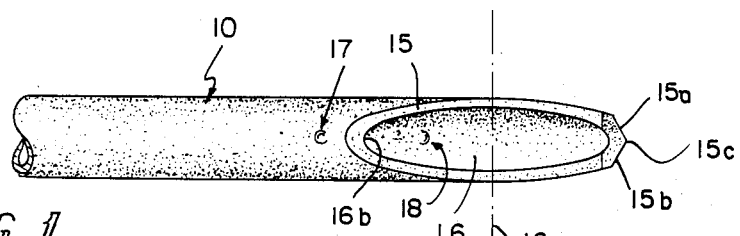
FIG. 1 is a top view of a subcutaneous implant needle in accordance with the invention.

The needle 10 shown in the drawing is formed from a hollow tube of rigid material, preferably one such as stainless steel that will provide a needle of rigid structure and may be easily cleaned and sterilized, either by immersion in alcohol or by exposure to high temperature. The tube may have an outer diameter of a significant fraction of an inch, for example, within a range from about $\frac{1}{8}$ of an inch to about $\frac{3}{8}$ of an inch (3.175 to 9.525 mm), and preferably about $\frac{1}{4}$ of an inch (6.35 mm). The wall should have sufficient thickness to provide enough rigidity that the needle will not bend in use where it is subjected to the manual force that may be exerted by a ranch hand. Where the tube is formed of stainless steel, such rigidity may be obtained with walls having a thickness of from about 0.010 of an inch to about 0.020 of an inch (0.254 to 0.508 mm).

Figure 2:
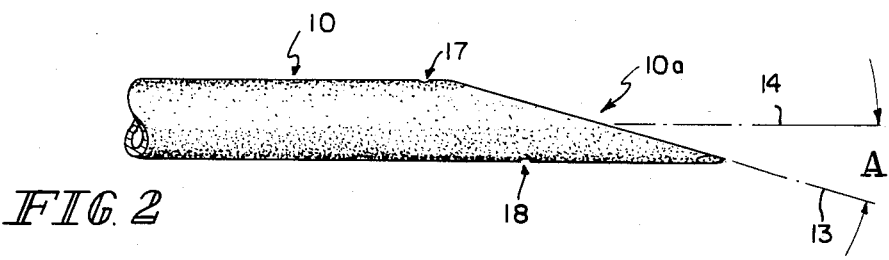
FIG. 2 is a side view of the needle of FIG. 1.
Figure 3:
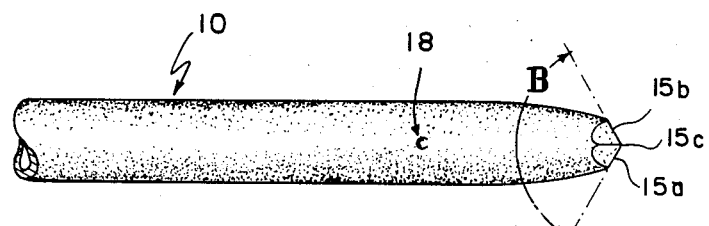
FIG. 3 is a bottom view of the needle of FIG. 1.

The forward end 10a of the needle is formed by grinding the hollow tube along a plane 13 at an acute angle A to the central axis 14 of the tube, as shown in FIG. 2. The acute angle A is preferably between about 15° and about 20°. Such grinding produces an elliptical end face having an elongated elliptical outer edge 15 and a similar inner edge defining an elliptical opening 16.

The forward extremity of the thus-ground tube is sharpened, as by honing over a length of several millimeters, preferably within a range from about 3 millimeters to about 5 millimeters. The forwardmost portion of the elliptical outer edge 15 is thus sharpened to define two substantially straight edge portions 15a and 15b that intersect at an obtuse angle B, preferably on the order of 120° to 135°. The overall width of the sharpened edge portions is less than the outside diameter of the tube and on a ¼ inch (6.35 mm) needle is preferably about 4 millimeters, and such edge portions extend rearwardly of their point of intersection a distance of about 1.6 millimeters.

After formation of the sharp cutting edges 15a and 15b, the forward end 10a of the needle is treated to remove the sharpness from and blunt the elliptical outer edge 15 of that end, especially along the diverging side edges adjoining the cutting edges 15a and 15b. One manner of rendering edge 15 unsharp is by sandblasting, and another manner is by tumbling in ceramic media. In sandblasting, the needle may be held in a holder which covers the sharpened edges 15a and 15b. The forward end 10a of the needle is othewise exposed to the sandblasting for a time sufficient to remove material from the side edge 15 that would otherwise provide a keen edge, and thus render edge 15 relatively unsharp or blunt. In addition, to further assist in the controlled implantation of implants into the animal, the needle is dimpled in two locations. Desirably, the first dimple 17 is located closely behind the opening 16, and the second dimple 18 is located within the area of the opening, rearward of the approximate center 16a of elliptical opening 16.

Where such subcutaneous implantation needle has an outside diameter of about ¼ inch (6.35 mm) and an inside diameter of about 7/32 of an inch (5.556 mm) and has its forward end cut along a plane 13 having an angle between 15° and 20°, the first dimple 17 may be located slightly more than 3/16 inch (4.76 mm) rearward of the rear edge 16b of the opening 16, and dimple 18 may be located about 3/16 inch (4.76 mm) forward of the rear edge 16b of the opening. The dimples are, preferably, located generally in a plane through the center of the needle and perpendicular to its cut end face, and extend into the tube a distance of about 0.015 inch to about 0.030 inch (0.38 mm to 0.76 mm).

The dimples will engage the implants prior to their explusion from the tube, prevent them from falling from the opening, and permit their expulsion to be controlled. Because implants may be curved, the location of the dimples in a plane through the center of the tube provides the probability of engagement of the ends of the implant by the dimples.

While this application discloses a specific preferred embodiment, other embodiments may be devised without departing from the spirit and scope of the invention as set forth in the following claims:

What is claimed is:

1. A subcutaneous implant needle for flexible implant pellets comprising a hollow metal tube having an outer diameter of a significant fraction of an inch and of sufficient rigidity to resist bending when subjected to manual force,
   one end of the tube being cut on a plane at an angle less than 30° with respect to the central axis of the tube to define an end face surrounding an elliptical opening and having an elliptical outer edge, said end being provided with a pair of dimples, one located a fraction of an inch forward of the rear edge of the opening and the other located a fraction of an inch behind the opening.

2. A subcutaneous implant needle comprising a hollow tube formed from stainless steel having an outside diameter of approximately ¼ inch (6.35 mm) and an inside diameter of approximately 7/32 inch (5.556 mm) and of sufficient rigidity to resist bending when subjected to manual force, one end of the tube being cut on a plane at an angle of from about 15° to about 20° with respect to the central axis of the tube to define an end face surrounding an elliptical opening and having an elliptical outer edge, the forward extremity of the cut portion being dressed to provide two substantially straight sharpened edge portions having a total width less than the outside diameter of the tube and forming an included angle of the order of 135°, the one end being provided with a pair of dimples, one dimple being located in the wall opposite the opening about 3/16 inch (4.76 mm) forward of the rear edge of the opening and another dimple being located about 3/16 inch (4.76 mm) rearward of the rear edge of the opening.

3. The subcutaneous implant needle of claim 2 wherein the side portions of the elliptical outer edge are abraded to blunt their sharpness.

4. An implant needle as in claim 3 in which the sharpened edge portions have a total width less than two-thirds the diameter of the tube.

5. An implant needle as in claim 1 in which the side portions of the elliptical outer edge of said end face are treated to dull the sharpness thereof.

6. An implant needle as in claim 5 in which said side edge portions are abraded to dull their sharpness.

7. An implant needle as in claim 5 in which the needles are sandblasted to dull the sharpness of said side edge portions.

8. A subcutaneous implant needle comprising a hollow metal tube having an outer diameter of a significant fraction of an inch and of sufficient rigidity to resist bending when subjected to manual force, one end of the tube being cut on a plane at an angle less than 30° with respect to the central axis of the tube to define an end face surrounding an elliptical opening and having an elliptical outer edge, the forward extremity of the cut end being sharpened over a width less than the diameter of the tube and the adjacent diverging side portions of the elliptical outer edge being treated to dull the sharpness thereof, said end also being provided with a pair of dimples, one located a fraction of an inch forward of the rear edge of the opening and the other located a fraction of an inch behind the opening.

9. An implant needle as in claim 8 in which the cut end of the tube is sandblasted to an extent sufficient to dull the sharpness of the side portions of the elliptical outer edge of said end face.

10. An implant needle as in claim 9 in which the sandblasting effect is confined to parts other than said sharpened edge portions.

11. The method of manufacturing a subcutaneous implant needle comprising
   providing a hollow tube of rigid material having a forward end,
   cutting the forward end of the hollow tube along a plane at an acute angle to its central axis to provide an elongated and closed outer edge,
   dimpling the hollow tube in two locations closely adjacent the rear edge of the opening, and
   abrading the cut end of the needle to blunt the sides of its elongated and closed outer edge.

12. The method of claim 11 wherein the tube is dimpled in a plane through the central axis of the tube and on opposite sides of the axis.

13. The method of manufacturing a subcutaneous implant needle comprising the steps of providing a hollow tube of rigid material having a forward end, cutting the forward end of the hollow tube along a plane at an acute angle to its central axis to provide an elongated and closed outer edge, dimpling the hollow tube in two locations closely adjacent the rear edge of the opening, abrading the cut edge of the needle to blunt the sides of its elongated and closed outer edge, dressing the foremost extremity of the cut end of the tube to form a sharp cutting edge thereon of a width less than the diameter of the tube and performing the abrading step so as to avoid dulling such sharp cutting edge.

14. The method of claim 13 in which the abrading is done by sandblasting after the sharpening step and while the sharp cutting edge is protected from the effect of sandblasting.

* * * * *